(12) United States Patent
Norman et al.

(10) Patent No.: US 8,904,849 B2
(45) Date of Patent: Dec. 9, 2014

(54) MULTI-DETECTOR GAS IDENTIFICATION SYSTEM

(75) Inventors: Mark L. Norman, Bridgewater, MA (US); Terence W. Sauer, Westport, CT (US); David R. St. Pierre, Waterbury, CT (US); Greger Andersson, Oxford, CT (US); Eric G. Diken, Danbury, CT (US)

(73) Assignee: Smiths Detection Inc., Danbury, CT (US)

( * ) Notice: Subject to any disclaimer, the term of this patent is extended or adjusted under 35 U.S.C. 154(b) by 0 days.

(21) Appl. No.: 13/612,567

(22) Filed: Sep. 12, 2012

(65) Prior Publication Data

US 2013/0046485 A1    Feb. 21, 2013

Related U.S. Application Data

(63) Continuation of application No. 11/905,414, filed on Sep. 28, 2007, now abandoned.

(60) Provisional application No. 60/847,660, filed on Sep. 28, 2006.

(51) Int. Cl.
 *G01N 33/00* (2006.01)
 *G06F 19/00* (2011.01)

(52) U.S. Cl.
 CPC .................................. *G01N 33/0073* (2013.01)
 USPC ......................................................... 73/23.2

(58) Field of Classification Search
 None
 See application file for complete search history.

(56) References Cited

U.S. PATENT DOCUMENTS

| | | |
|---|---|---|
| 6,732,032 B1 * 5/2004 | Banet et al. | 701/31.4 |
| 2003/0176804 A1 9/2003 | Melker | |
| 2004/0005715 A1 * 1/2004 | Schabron et al. | 436/104 |
| 2005/0092914 A1 5/2005 | Miller et al. | |
| 2005/0173629 A1 8/2005 | Miller et al. | |
| 2006/0008051 A1 1/2006 | Heaton et al. | |

OTHER PUBLICATIONS

D.M. Wilson et al., "Rank Extraction in Tin-Oxide Sensor Arrays", Sensors & Actuators B, 2000, 199-210, 62, Elsevier, U.S.A.
Final Office Action U.S. Appl. No. 11/905,414 dated Mar. 13, 2012.
Non-Final Office Action U.S. Appl. No. 11/905,414 dated Aug. 26, 2011.

* cited by examiner

*Primary Examiner* — Hezron E Williams
*Assistant Examiner* — Gregory J Redmann
(74) *Attorney, Agent, or Firm* — Foley & Lardner LLP

(57) ABSTRACT

A novel gas analysis system and method of identifying analytes in a gas sample are provided. The system uses multiple gas analysis technologies and uses the combined qualitative and quantitative data obtained from the multiple gas analysis technologies to analyze a gas sample.

29 Claims, 8 Drawing Sheets

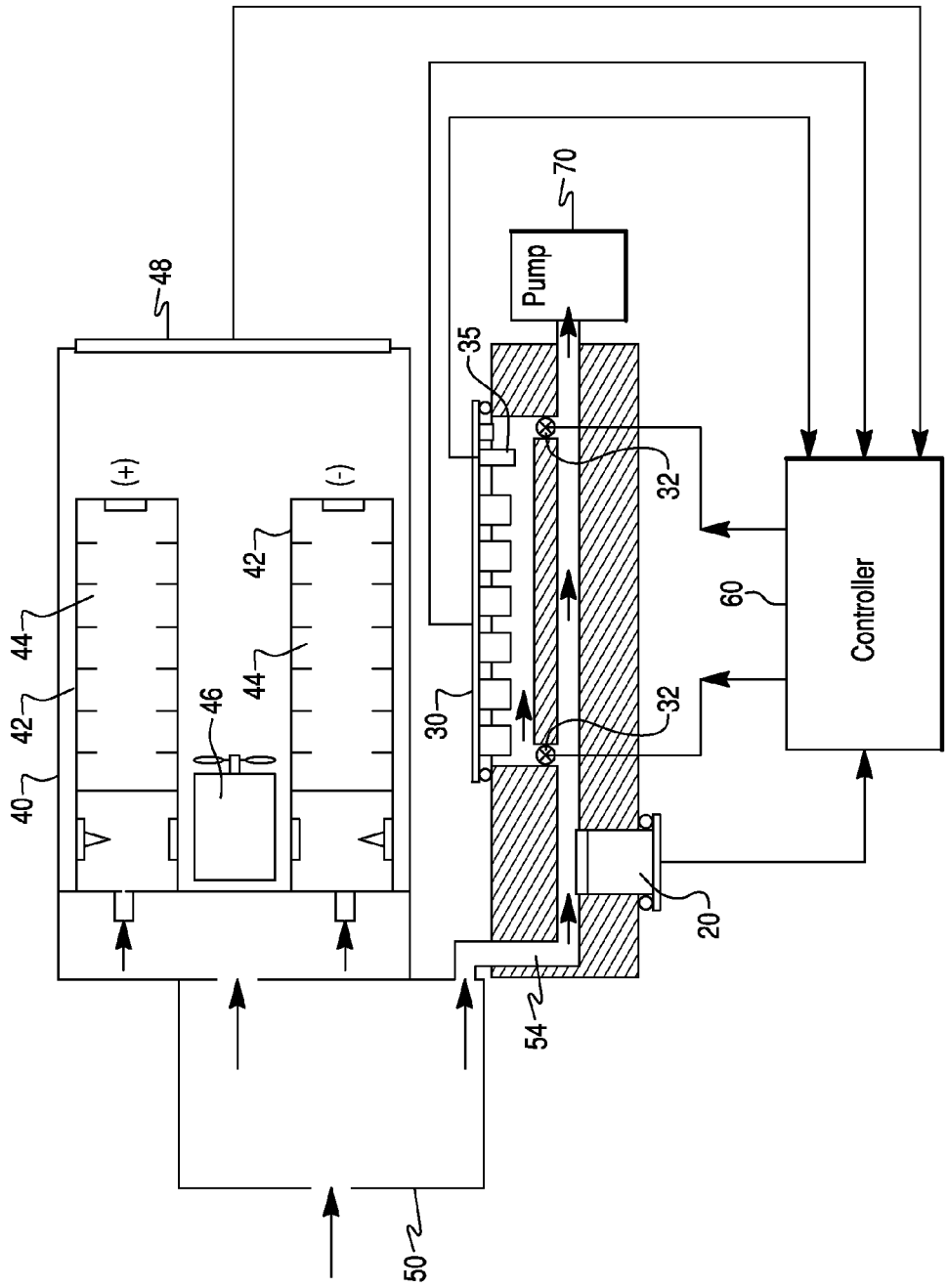

MULTI-DETECTOR GAS IDENTIFICATION SYSTEM

RELATED APPLICATIONS

This application is a continuation application of U.S. application Ser. No. 11/905,414 filed Sep. 28, 2007 which claims priority to U.S. provisional application 60/847,660, filed on Sep. 28, 2006, the contents of which are incorporated by reference.

SUMMARY OF THE INVENTION

There is a need in the art for a system capable of identifying and quantifying a wide variety of analytes. One embodiment provides a gas analysis system comprising a plurality of gas analysis units and a computer system, wherein the plurality of gas analysis units are in fluid contact with a single gas sample, wherein the plurality of gas analysis units comprises a photoionization detector (PID), a chemical sensor array, and ion mobility spectrometers (IMS), wherein data produced by each of the gas analysis units is analyzed individually and/or in parallel and the data is characteristic of an analyte, and wherein the qualitative and quantitative data from each of the gas analysis units are multiplexed to identify the analyte.

BRIEF DESCRIPTION OF THE DRAWINGS

FIG. 1B is a block diagram of an another exemplary gas analysis system combining a PID, a metal oxide chemical sensor (MOS) array and an IMS on a single platform and in simultaneous fluid contact with a single gas sample, where further details of the IMS are illustrated.

DETAILED DESCRIPTION

Figure 1A:
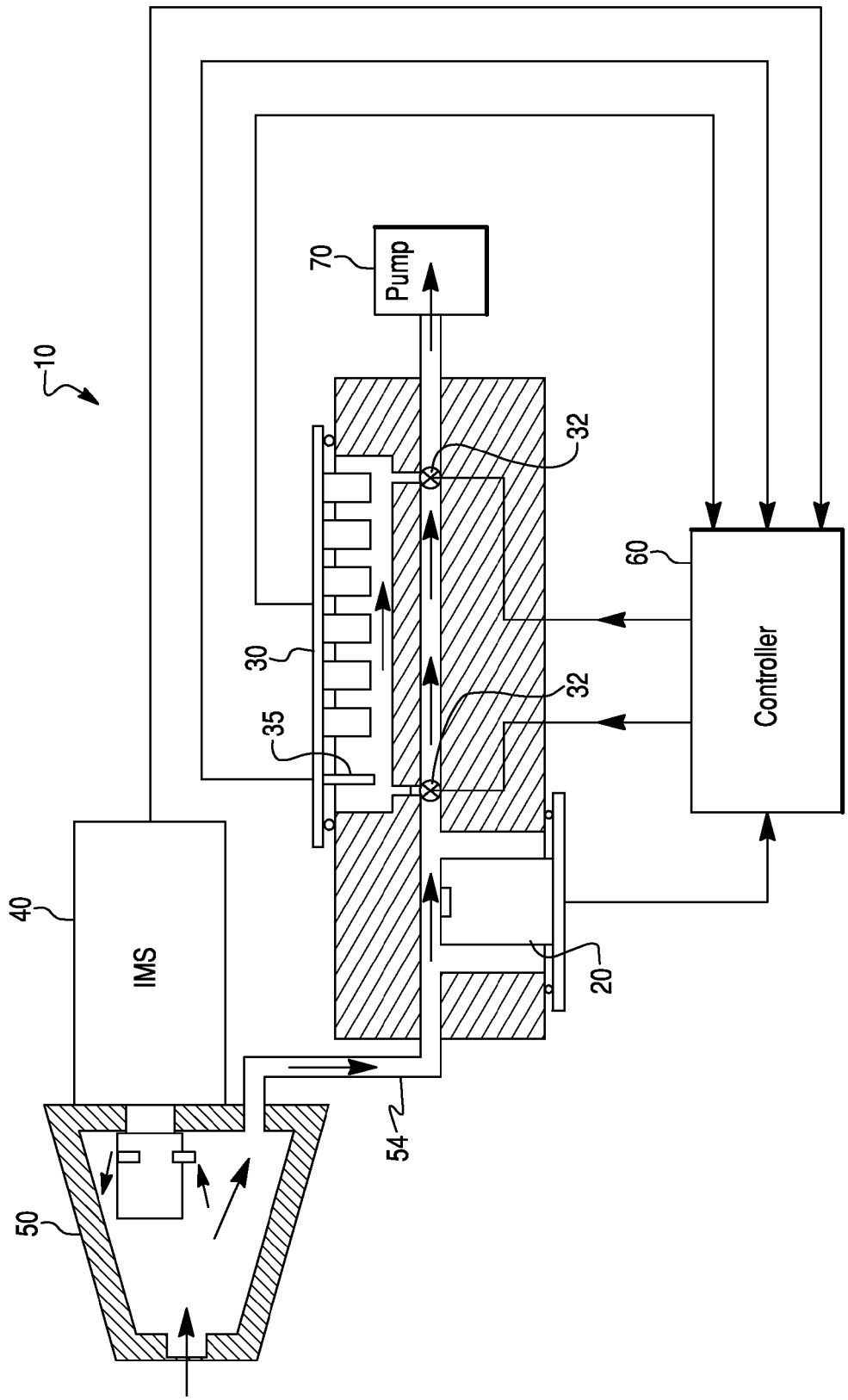
FIG. 1A is a block diagram of an exemplary gas analysis system combining a PID, a metal oxide chemical sensor (MOS) array and an IMS on a single platform and in simultaneous fluid contact with a single gas sample.

There is a need in the art for a system capable of identifying a variety of analytes that can be present in a gas sample such as, for example, toxic industrial chemicals (TIC), chemical warfare agents (CWAs), irritants, and simulants. An analyte also can be present as a solid or liquid sample. In such cases, the analyte can be made gaseous to facilitate analysis.

FIG. 1 shows an exemplary embodiment of a gas analysis system. The gas analysis system can include a plurality of gas analysis technologies and the data output of the plurality of gas analysis technologies can be used to identify one or more target analytes present in a gas sample. The system can use a common inlet and common sample flow path to allow the same gas sample to be analyzed by the gas analysis technologies. For example, the common inlet 50 may comprise an inlet chamber.

The gas analysis technologies can be incorporated into a system as gas analysis units, which can be individually selected and upgradeable. A redundant gas analysis technology also can be used. A gas analysis technology includes, but is not limited to, an ion mobility spectrometer (IMS), a chemical sensor, a chemical sensor array, a photoionization detector (PID), a radioactivity detector, a gas chromatograph (GC), a mass spectrometer (MS), a GC-MS, an optical spectrometer (including, e.g., infrared (IR), Raman, etc.) or a biosensor (including, e.g., fluorescence). Any embodiment of such gas analysis technologies known in the art can be used. In one embodiment, as shown in FIG. 1, the gas analysis system 10 comprises a PID 20, a chemical sensor array 30, and a dual channel IMS 40. The system also can include standard four-gas meter capabilities that can measure inflammable gases in terms of their lower explosive limit (LEL), as well as levels of carbon dioxide, oxygen, and hydrogen sulfide.

A chemical sensor array can be comprised of one or more of any of the following: a semiconductor sensor (e.g., a metal oxide chemical sensor (MOS) array), an electrochemical sensor (EC), (e.g. a cermet sensor), a surface acoustic wave (SAW) sensor, an optical vapor sensor, chemiresistor sensors, or a conductive polymer sensor. A chemical sensor array can be comprised of a plurality of one type of sensor, any combination of different types of sensors, including a plurality of one or more different types of sensors. In one embodiment, a chemical sensor array can be comprised of any metal oxide sensor, including, but not limited to a tin oxide ($SnO_2$) sensor. Any suitable type of metal oxide sensor can be used, such as, for example, a liquefied petroleum gas (LP) sensor, a volatile organic compound (VOC) sensor, or a toxic air contaminant gas sensor. In another embodiment, a metal oxide sensor can be a Taguchi Gas Sensor (TGS, Figaro USA, Inc., Glenville, Ill.). In a further embodiment a sensor can be a Figaro TGS 2600-series sensor (2600, 2602, 2610, 2620, etc.).

A chemical sensor array can contain between 2 and 4, between 2 and 6, or between 2 and 10 sensors, for example. In one embodiment, an array contains 6 sensors.

The chemical sensor array gas analysis unit can be included in a common flow path 54 (the arrows in FIGS. 1A and 1B illustrate the flow) that delivers a portion of the sample stream to each gas analysis unit or technology simultaneously while permitting each detector to function individually and to be individually controlled. A gas analysis system can include one or more valves 32 associated with a chemical sensor array that can isolate a chemical sensor array from the sample stream upon analyte exposure to prevent saturation of the individual chemical sensors. One or more valves are capable of isolating the chemical sensor array from the gas sample by diverting the sample flow array from the chemical sensor array. The one or more valves can be a set of valves. The valves can be actuated in a first position or a second position in response to the amount of analyte detected by an IMS, a PID and/or the chemical sensor array. In a first position, the valves allow fluid communication of a gas sample with the chemical sensor array. In a second position, the valves prevent fluid communication of a gas sample with a chemical sensor array. A valve or valves can be in communication with a control mechanism, such as controller 60, for actuating the one or more valves. The control mechanism can be computer controlled and can use operation logic for achieving proper exposure of the chemical sensor array to a gas sample. In one embodiment, the system operates with the valves in the first position to allow the chemical sensor array to detect analytes in the background air. Once the chemical sensor array senses the presence of one or more analytes and produces a sufficient amount of signal to identify the one or more analytes based on the kinetics of the individual chemical sensor responses, the system autonomously operates the valves to be arranged in the second position and processes the data, during which time the other gas analysis technologies (e.g., IMS and PID) continue to monitor the sample stream. Following the chemical sensor array detection event, the system again operates the valves to be arranged in the first position to allow the chemical sensor array to recover, but will alternate between valve positions if the background air is not sufficiently clear. This operation serves to minimize both the response time for sample identification and the recovery time of the chemical sensors by limiting the exposure of the sensor array to a sample. For example, a MOS array will produce sufficient data for sample identification within 1-30 seconds after initial exposure and will recover to baseline within approximately 30 seconds to approximately 5 to 10 minutes.

A chemical sensor array can be controlled by an operation logic. The operation logic can enable a chemical sensor array to detect analytes with a fast response time and in concert with other gas analysis technologies in a gas analysis system. In one embodiment a chemical sensor array analysis time can be from approximately 1 to approximately 30 seconds. Operation logic also can control exposure of a chemical sensor array to a sample such that the amount of an analyte in contact with a chemical sensor array is sufficient for identification, but that saturation of the array is avoided and recovery time is minimized.

FIG. 1B illustrates another exemplary embodiment of a gas analysis system, where like reference numerals illustrate the same features as in the embodiment illustrated in FIG. 1A. FIG. 1B illustrates the components of the dual channel IMS 40 in further detail. The dual channel IMS 40 comprises dual ion mobility spectrometers 42, where each of the spectrometers 42 includes a drift cell 44. The dual channel IMS 40 also comprises a fan 46 and dopant 48 as shown in FIG. 1B.

Figure 2:
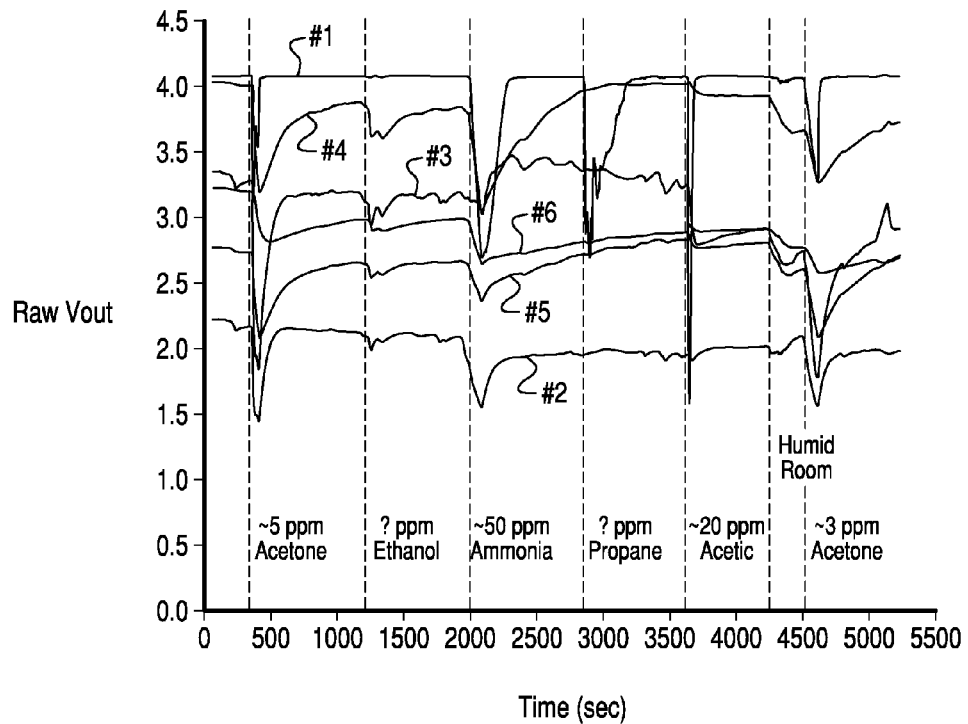
FIG. 2 is a graph showing raw output voltage (Vout) versus time for gas sample measurements obtained during an ambient air controlled contamination experiment using an array of six MOS employed in a functional prototype of the exemplary system described in FIG. 1.

A chemical sensor array operation logic can process one or more time-dependent chemical sensor signals to produce a multi-channel array pattern, which can be used to identify an analyte. FIG. 2, for example, shows time-dependent responses of a six-sensor MOS array to various gas samples. For FIG. 2, the array uses 2600-series $SnO_2$ Taguchi Gas Sensors (TGS, Figaro USA, Inc., Glenville, Ill.) operated at the following conditions (operating voltages, Vop): sensor 1=TGS 2610 at 4.5 Vop, sensor 2=TGS 2602 at 3.5 Vop, sensor 3=TGS 2600 at 3.5 Vop, sensor 4=TGS 2600 at 3.0 Vop, sensor 5=TGS 2610 at 3.0 Vop, and sensor 6=TGS 2610 at 2.5 Vop. The identities of the released analytes are given in the Figure, and the concentrations (parts per million, ppm) were determined from the PID measurements referenced in FIG. 3.

Chemical sensors within an array can be the same or different. Sensors within an array can be operated using different parameters to obtain data sufficient to identify an analyte or to propose a list of possible analytes (a "hit list"). For example, an individual MO sensor in a MOS array can operate at a fixed temperature (fixed operating voltage, Vop) or the temperature/voltage can be temporally modulated and multiple data points obtained from a single sensor. In one embodiment, data can be collected using multiple MO sensors operating at different, fixed temperatures. A change in MO sensor response as a function of temperature can provide data useful in identifying an analyte. For example, a chemical sensor array can include multiple sensors, where each of the sensors operates at a different, fixed temperature. In one embodiment, a gas analysis unit comprises multiple metal oxide sensors. The multiple metal oxide sensors can be $SnO_2$ sensors, each operating at a different, fixed temperature and voltage.

Figure 4:
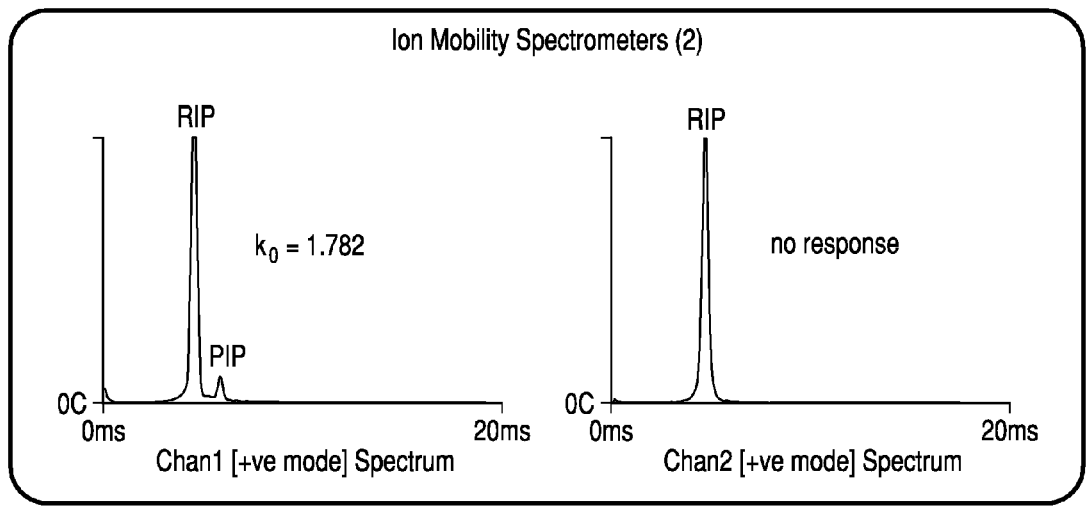
FIG. 4 is a graph showing representative data for PID, MOS, and IMS detectors for a single sample of 5000 ppm benzene obtained using a functional prototype of the exemplary system described in FIG. 1.
Figure 4:
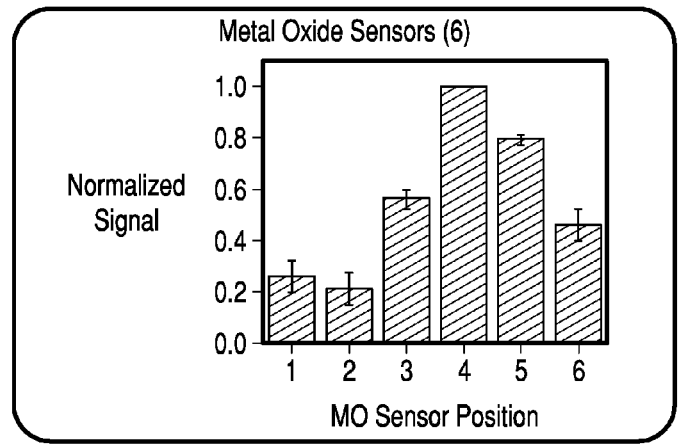
Figure 4:
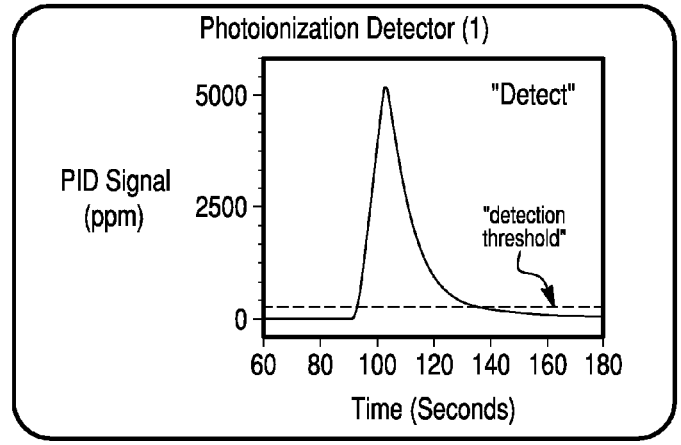
Figure 5:
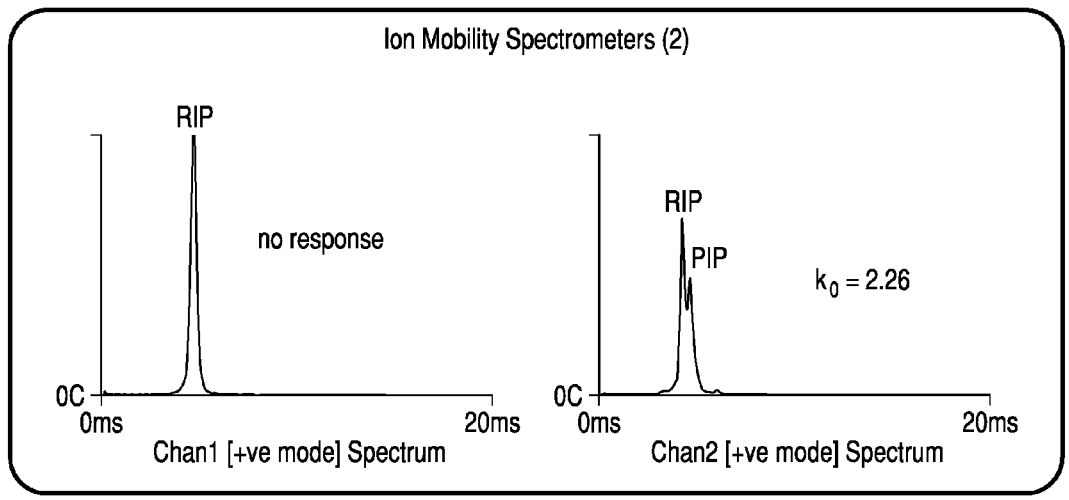
FIG. 5 shows representative data for PID, MOS, and IMS detectors for a single sample of 150 ppm diborane obtained using a functional prototype of the exemplary system described in FIG. 1.
Figure 5:
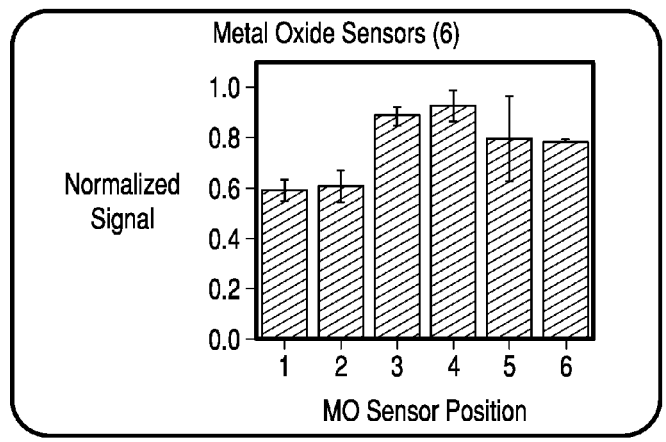
Figure 5:
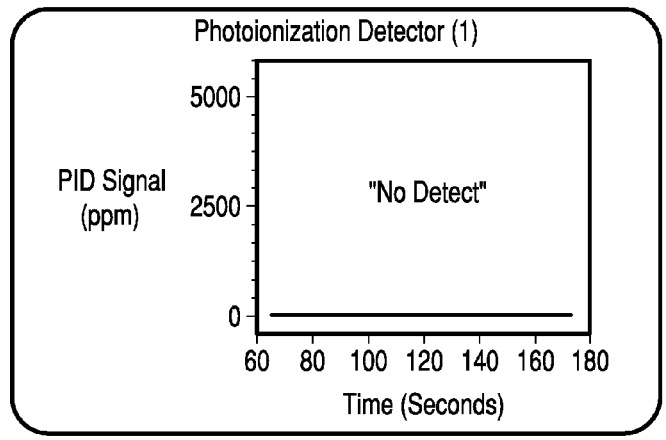

Kinetic information associated with the sensing mechanism of a chemical sensor also can be used as output data for identifying an analyte and can be used for assessing array status. A gas analysis system can monitor rate of change of the MOS responses (i.e., dVi/dt or any change between two or more data points within the data array over the course of the measurement), which can be used to autonomously monitor the MOS array stability. Using this information, one can set a reference MOS baseline (Vo) based on dVi/dt, monitor the dVi/dt signal or deflection from Vo as an indicator of sensor response, and transform mathematically the time-dependent response of each sensor to produce a response signal for each sensor channel. For example, FIGS. 4 and 5 show six-channel MOS array patterns for benzene and diborane, respectively, in which the signal for each sensor channel monitored at 5 Hz is processed over a predetermined time window. A gas analysis system also can be configured to allow the ability to set multiple temperatures for a MOS allowing customization for different sets of analytes. In FIG. 4, the two IMS spectrometers (Smiths Detection) refer to the positive and negative ion mode responses, and the reactant ion peaks (RIP) are noted. The reduced mobility ($k_0$) for the positive mode product ion peak (PIP) is also given. The MOS array pattern was calculated from the time-dependent raw data, using $SnO_2$ TGS sensors operated at the following conditions: sensor 1=TGS 2600 at 4.5 Vop, sensor 2=TGS 2620 at 4.5 Vop, sensor 3=TGS 2600 at 5.0 Vop, sensor 4=TGS 2620 at 5.0 Vop, sensor 5=TGS 2610 at 4.5 Vop, and sensor 6=TGS 2610 at 5.0 Vop. The 10.6 eV PID data illustrates that the analyte is detectable above the preset threshold during the course of the measurement. In FIG. 5, the reduced mobility ($k_0$) for the negative mode product ion peak (PIP) is given. The MOS array is the same as in FIG. 4. The 10.6 eV PID data illustrates that the analyte is not detectable above the preset threshold during the course of the measurement.

A system also can include a relative humidity (% RH) sensor such as the sensor 35 shown in FIGS. 1A and 1B. Any suitable % RH sensor can be used. In one embodiment the % RH sensor can be temperature-compensated. In another embodiment, a % RH sensor can be a capacitive thin film sensor.

Figure 3:
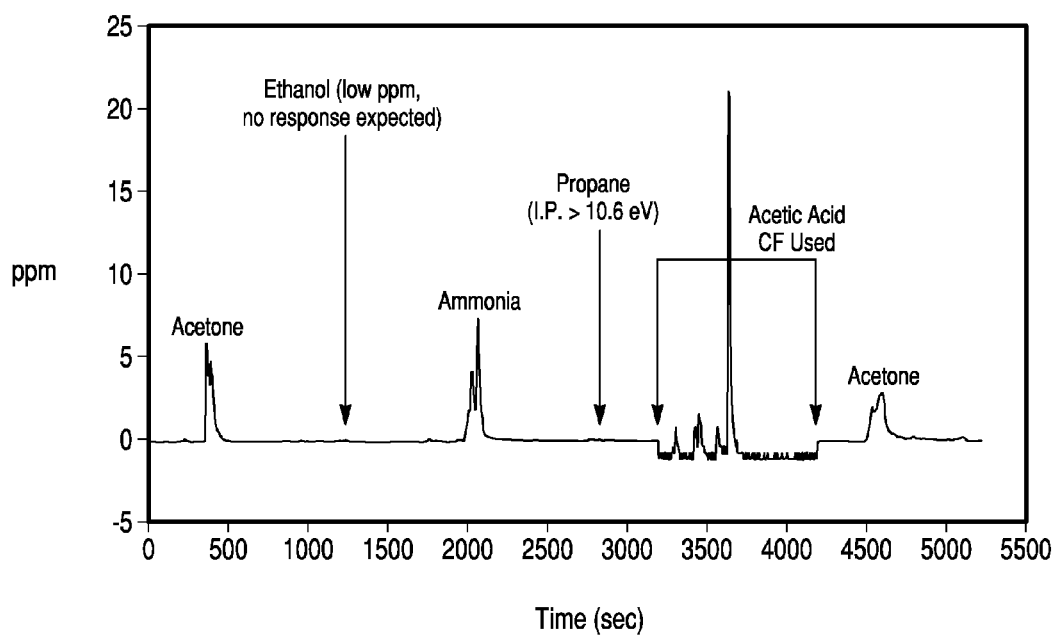
FIG. 3 is a graph showing the PID data obtained during the same experiment referenced in FIG. 2.

A system also can include a PID 20. The voltage output (Vout) of the PID can be monitored periodically or continuously. The voltage can be monitored at 0.2 Hz, 1 Hz, 5 Hz, 10 Hz, or any other practical rate. In one embodiment, the PID Vout is continuously monitored at 1 Hz, as illustrated in FIG. 3, or at an optimum rate based on analog-to-digital converter (A/D) delay times. In another embodiment, the PID incorporates a 10.6 eV ionization source. A PID can be adjusted with a user controlled gain. The system can access a database containing correction factors (CF) for target analytes, such as, for example, target analytes that a system can be programmed to detect. A PID can calculate sample concentration using, for example, [((Vout−PID0)/PIDCAL)*CF], where PID0 is a baseline voltage that is determined autonomously by the system or manually by the user, and PIDCAL is a calibration response factor (mV/ppm) that is specific for each PID. FIG. 3 shows exemplary PID readings from a controlled contamination ambient air monitoring experiment employing a functional prototype of the exemplary system described in FIG. 1 during which low levels of acetone, ethanol, ammonia, propane and acetic acid were released. Any suitable PID can be used having a detection range of from approximately 1 to approximately 5000 ppm. In one embodiment, the PID can be a Black Label piD-Tech PID sensor unit (Baseline-Mocon, Inc, Lyons, Colo.). The PID data in FIG. 3 was obtained with the Black Label 10.6 eV piD Tech PID module (Baseline-Mocon, Lyons, Colo.) simultaneously with the MOS data during the experiment referenced in FIG. 2. The concentration (ppm) values on the ordinate axis were calculated in real time using analyte correction factors (CF, as noted) that were programmed into the system computer of the prototype.

In one embodiment, the system can autonomously adjust a second and subsequent "corrected" PID reading based on the identity information to enable continuous air monitoring and quantification by the system.

The chemical sensor array and PID detector can be contained in a chamber that allows the PID to be continuously exposed to a gas sample during operation of the system.

An IMS can be a single IMS or a dual-channel IMS having two IM spectrometers that are adapted to monitor positive and negative mode ions simultaneously. An IMS can function at approximately room temperature ("cold IMS") or at elevated temperatures ("hot IMS"). An IMS can use any suitable reagents or dopants, including, for example, ammonia, acetone, dimethylsulfoxide, nicotinamide, nonylamine, hydrazine, monomethyl hydrazine, dimethylhydrazine or water.

The system can include methods of noise reduction and signal amplification.

A gas analysis system can be self-contained and portable and, in one embodiment, man-portable. In another embodiment, the system can be handheld. The system can include a battery and/or it can be battery powered. In a further embodiment the system is ruggedized and can used in a range of ambient conditions. The system can be capable of automatic clearing and resetting of the system and gas analysis units.

An analysis cycle can be less than 20 minutes, less than 15 minutes, less than 10 minutes, less than 5 minutes, less than 2 minutes, less than 1 minute, less than 30 seconds, less than 15 seconds, less than 10 seconds, less than 5 seconds, less than 3 seconds, or less than 1 second. In one embodiment, an analysis cycle can be less than 3 seconds.

A system can include one or more compressors or pumps 70, such as shown in FIGS. 1A and 1B. A compressor or pump can draw a gas sample through the system, providing a portion of the same gas sample to each gas analysis unit in the system.

Any suitable sample collection system can be used. For example, in one embodiment, the sample collection system can include a flexible wand that interfaces with an inlet port. The system can include a means for preventing introduction of liquid into the system, such as, for example, a water trap. A system can be mounted on a tripod or function free-standing so that the system is capable of constant monitoring applications.

A system can be capable of collecting a sample that can be further analyzed at a remote site, such as, for example, a laboratory.

The system can include a computer system. The computer system can be on-board or remote, connected via hard wire or wireless or a combination of hard wire and wireless. In one embodiment, the computer system is on-board. The computer system may be part of the controller 60 (See FIGS. 1A and 1B) or may be separate therefrom.

The computer system can include at least one memory. The memory can be any type of computer memory or any other type of electronic storage medium that is located either internally or externally to the system, such as, for example, read-only memory (ROM), random access memory (RAM), compact disc read-only memory (CDROM), electro-optical memory, magneto-optical memory, or the like. As will be appreciated based on the following description, the memory can, for example, be programmed using conventional techniques known to those having ordinary skill in the art of computer programming. The actual source code or object code for carrying out the steps of, for example, a computer program can be stored in the memory.

The computer system can also include at least one processor, for example, to execute the computer program stored in the memory. The processor can be any known processor, such as, for example, any type of microprocessor. However, those of ordinary skill in the art will recognize that the system can be any combination of hardware, software, and/or firmware.

The computer system can be configured to monitor and control the operation of the system and/or to analyze response data obtained from the gas analysis units. To facilitate analysis of a gas sample, the computer system can include software and hardware for identifying target analytes using response data obtained from a sample. For example, software in the computer system can be coded to interpret obtained data (e.g., chemical sensor array response, photoionization response, IMS spectrum peak location, peak height, peak area) using comparison to a database or library of known responses that correspond to known target analytes and to known chemical families or functional groups. In one embodiment, the computer system can include, for example, a spectral library (database) of known IMS spectra for various functional groups and chemicals. In another embodiment, the computer system can include a database of chemical sensor array pattern signatures for known target analytes. In a further embodiment, the computer system can include a database of ionization potentials and PID correction factors for known target analytes. In yet another embodiment, the computer system can contain one or more databases providing an IMS spectral library, chemical sensor array pattern signatures, and ionization potentials of known target analytes. In another exemplary embodiment, the computer system can provide an indication of the degree of certainty or percentage match of the identified analyte with the unknown analyte present in a gas sample.

The computer system also can include a graphical user interface for displaying information. The graphical user interface can display, for example, a list of functional groups or chemicals from the databases that correspond to the response data obtained for the unknown analyte, including an International Union of Pure and Applied Chemistry (IUPAC) chemical and a common name of the identified compound. In addition, the computer system can include user input systems, such as a keyboard or mouse, touchpad, joystick, or other control mechanism to allow the user to interact with the computer system. Furthermore, the computer system can include hardware and/or software to allow the user to manipulate information provided on the graphical user interface. The computer system can include log and data storage capability including, for example, date, time, user identification, and system status at the time of sample analysis. The computer system can include global positioning system hardware and software that can record the location of a sample collection.

As discussed above, a gas analysis system can be an all-inclusive unit that functions as a single unit. Alternatively, an all-inclusive unit can be networked with other units that can be placed in different locations. In another embodiment, one or more systems containing the desired gas analysis units can be networked to a remote computer, which performs control and/or analysis functions. A system can use wireless technology to communicate with a central controller when used remotely or a part of a network.

The computer system also can include a network connection for connecting the system to one or more networks (e.g., intranets or internets) or other systems. The network connection can be any type of network connection, such as, for example, an Ethernet connection, to a remote computer system, network or the like, or any other form of connection (e.g., a RS-232 connection, an optical link, a wireless connection, or the like) over which information can be communicated.

A system can be used to detect a wide variety of analytes. In one embodiment, the system is used to detect and identify priority TICs and CWAs and is programmable to detect and/or identify other vaporous or aerosolized chemical or biological agents of interest. Other vaporous and/or aerosolized materials that may be detected and/or identified by the system can be, but are not limited to, any specific chemical from the general classes of hydrocarbons, alcohols, aldehydes, ketones, aromatics, peroxides, esters, ethers, carbonates, nitrates, phosphates, sulfates, sulfides, halides, azides, as well as explosives, drugs, CWAs and simulants, BWAs and simulants, and combinations thereof.

TICs that can be detected and/or identified include, but are not limited to, acetone, acrylonitrile, ammonia, benzene, butane, carbon monoxide, chlorobenzene, mono-, di-, and tri-methyl amine, hexane, methyl hydrazine, hydrogen cyanide, hydrogen sulfide, methane, methyl ethyl ketone, m-xylene, pepper spray (capsaicin), phosgene, propane, trichloroethylene, acrolein, ethanol, formaldehyde, isopropanol, methanol, phosphine, 1,1,1-trichloroethane, vinyl chloride, chlorine, ethylene oxide, hydrogen chloride, hydrogen fluoride, phosphorus trichloride, sulfur dioxide, sulfuric acid, methyl caproate, tetrachloroethylene, acetic acid, fluorine, hydrogen bromide, nitric acid, styrene, arsine, boron trichloride, boron trifluoride, carbon disulfide, sulfur hexafluoride, diborane, diethyl sebacate, nitrogen dioxide, trifluoronitrosyl methane, tungsten hexafluoride, carbon dioxide, and combinations thereof.

Explosives that can be detected and/or identified include, but are not limited to, 2-amino-4,6-dinitrotoluene, 4-amino-2,6-dinitrotoluene, ammonal, ammonium nitrate, black powder, 2,4-dimethyl-1,3-dinitrobutane, 2,4-dinitrotoluene, ethylene glycol dinitrate, forcite 40, GOMA-2, hexanitrostilbene, 1,3,5,7-tetranitro-1,3,5,7-tetrazacyclooctane (HMX), mononitrotoluene, nitroglycerine, pentaerythritol tetranitrate (PETN), 1,3,5-trinitro-1,3,5-triazacyclohexane (RDX), semtex-A, Semtex-H, smokeless powder, trinitro-2,4,6-phenylmethylnitramine tetryl (Tetryl), 2,4,6-trinitrotoluene (TNT), trilita, and 1,3,5-trinitrobenzene and combinations of these compounds. In one embodiment, the explosive which are collected are 1,3,5-trinitro-1,3,5-triazacyclohexane, pentaerythritol tetranitrate, 2,4,6-trinitrotoluene, trinitro-2,4,6-phenylmethylnitramine tetryl, nitroglycerine, ammonium nitrate, 3,5,7-tetranitro-1,3,5,7-tetrazacyclooctane, and combinations thereof.

Chemical warfare agents and other toxins that can be detected and/or identified include, but are not limited to amiton (VG), arsine, cyanogen chloride, hydrogen chloride, chlorine, diphosgene, PFIB, phosgene, phosgene oxime, chloropicrin, ethyl N,N-dimethyl phosphoramicocyanidate (Tabun), isopropyl methyl phosphonofluoridate (Sarin), pinacolyl methyl phosphonefluoridate (Soman), phosphonofluoridic acid, ethyl-, isopropyl ester (GE), phosphonothioic acid, ethyl-, S-(2-(diethylamino)ethyl) O-ethyl ester (VE), phosphonothioic acid, methyl-, S-(2-(diethylamino)ethyl) O-ethyl ester (VM), distilled mustard, ethyldichloroarsine, lewisite 1, lewisite 2, lewisite 3, methyldichloroarsine, mustard-lewisite mixture, mustard-T mixture, nitrogen mustard 1, nitrogen mustard 2, nitrogen mustard 3, phenyldichloroarsine, phosgene oxime, sesqui mustard, adamsite, aflatoxin, botulinus toxin, ricin, saxitoxin, trichothecene mycotoxin, methylphosphonothioic acid S-(2-(bis(1-methylethyl) amino)ethyl) O-ethyl ester (VX), cyclohexyl methylphosphonofluoridate (GF), and combinations thereof.

Biological agents that can be detected and/or identified include, but are not limited to *Bacillus anthracis* (anthrax), *Clostridium botulinum* toxin, *Yersinia pestis* (plague), variola major (smallpox), *Francisella tularensis* (tularemia), and *Ricinus communis* (ricin).

A target analyte can be detected and identified at less than or equal to the Immediately Dangerous to Life and Health (IDLH) concentration. In one embodiment, an analyte can be detected and identified at less than or equal to approximately 50% of the IDLH concentration, less than or equal to approximately 25% of the IDLH concentration, or less than or equal to approximately 10% of the IDLH. Table A lists some exemplary TICs that can be detected and identified along with their 10% IDLH ((1/10) IDLH) concentrations. In some embodiments, some of the target analytes may be identified at greater than 50% IDLH concentration.

TABLE A

| TIC | 1/10 IDLH | TIC | 1/10 IDLH |
|---|---|---|---|
| Acetone | 250 ppm | Arsine | 300 ppb |
| Acrolein | 200 ppb | Chlorobenzene | 100 ppm |
| Acrylonitrile | 8.5 ppm | Hexane | 110 ppm |
| Ammonia | 30 ppm | Hydrogen bromide | 3 ppm |
| Benzene | 50 ppm | Methane | 1000 ppm |
| Propane | 210 ppm | Methyl ethyl ketone | 3000 ppm |
| Carbon disulfide | 50 ppm | m-xylene | 90 ppm |
| Chlorine | 1 ppm | Butane | 1000 ppm |
| Diborane | 1.5 ppm | Tungsten Hexafluoride | 30 ppm |
| Ethylene oxide | 800 ppm | Acetic Acid | 50 ppm |
| Fluorine | 2.5 ppm | Isopropanol | 200 ppm |
| Formaldehyde | 2 ppm | Methanol | 600 ppm |
| Hydrogen cyanide | 5 ppm | Dimethylamine | 50 ppm |
| Hydrogen chloride | 5 ppm | Phosphine | 5 ppm |
| Hydrogen fluoride | 3 ppm | Styrene | 70 ppm |
| Hydrogen sulfide | 10 ppm | Tetrachloroethylene | 15 ppm |

TABLE A-continued

| TIC | 1/10 IDLH | TIC | 1/10 IDLH |
|---|---|---|---|
| Nitric acid | 2.5 ppm | Trichloroethane 1,1,1 | 700 ppm |
| Phosgene | 20 ppb | Trichloroethylene | 100 ppm |
| Phosphorus trichloride | 2.5 ppm | Vinyl chloride | 10 ppm |
| Sulfur dioxide | 10 ppm | | |
| Ethanol | 3300 ppm | | |
| Boron Trichloride | 2.5 ppm | | |
| Boron Trifluoride | 2.5 ppm | | |
| Carbon Monoxide | 120 ppm | | |
| Diethyl methyl phosphonate | 25 ppm* | | |
| Ethyl Mercaptan (ethanethiol) | 50 ppm | | |
| Methyl hydrazine | 2 ppm | | |
| Nitrogen Dioxide | 2 ppm | | |
| Sulfuric Acid | 15 mg/m3 | | |
| Thionyl chloride | 10 ppm* | | |

Target analytes can be detected and identified using data supplied by the gas analysis technologies of a system. As discussed above, each gas analysis technology includes one or more detectors capable of providing a signal or data output in response to an analyte. Output of each detector (e.g., response data) can be recorded by a computer. Each gas analysis technology can provide qualitative and quantitative response data that are characteristic of an analyte. In some cases, the response data from a detector will be the same for different analytes and in other cases, the response data from a detector will be different for different analytes. Using response data from more than one gas analysis technology can be useful to differentiate analytes having the same response data, because analytes having the same response data in a first gas analysis technology often will not have the same response data in a second gas analysis technology.

The qualitative and/or quantitative response data from the gas analysis technologies and the detectors and sensors of each of the gas analysis technologies can be combined (or "multiplexed") using a novel algorithm that can identify an analyte in a sample. The algorithm can multiplex data from a plurality of gas analysis technologies to provide the chemical identity of an analyte or to provide a class of chemical of an analyte.

An IMS response comprises of an ion spectrum from which measurable peaks can be located and normalized to reduced mobility ($k_0$) space to account for parameters such as temperature and pressure. In one embodiment, the $k_0$ values and their associated intensities can be compared against known peak "windows" to determine whether the measured spectrum is consistent with one or more of the known analytes. The IMS peaks also can provide semi-quantitative information based on the measured intensities. The peak window of a known analyte, provided in, for example, a database provided in the computer system, can be compared to a peak window of an unknown analyte and the identity of an analyte or group of potential analytes can be determined.

A PID response is a voltage output that can generate a binary metric that indicates whether one or more of the known analytes could be present according to their known ionization potentials (relative to the PID bulb energy). These ionization potentials are inherently characteristic of the analyte and can be used in concert with response data from the other gas analysis technologies to identify the analyte. Furthermore, a PID response can be converted to a concentration using a pre-set calibration coefficient (PIDCAL) and a correction factor (CF) for the analyte following its identification.

A chemical sensor array response is an array of signals that can be produced using any suitable analysis method known in the art. In one embodiment, a chemical sensor array response can be produced by processing and, optionally, integrating a time-dependent voltage output for each sensor upon exposure to the analyte to obtain qualitative and quantitative information. This array pattern can be further processed using pattern recognition techniques, such as, for example, rank extraction (Wilson, D. M., et al, "Rank Extraction in Tin-Oxide Sensor Arrays," Sensors and Actuators B, 62, pp. 199-210 (2000)), or as otherwise known in the art to determine whether a measured response pattern is consistent with one or more known target analytes.

Figure 6:
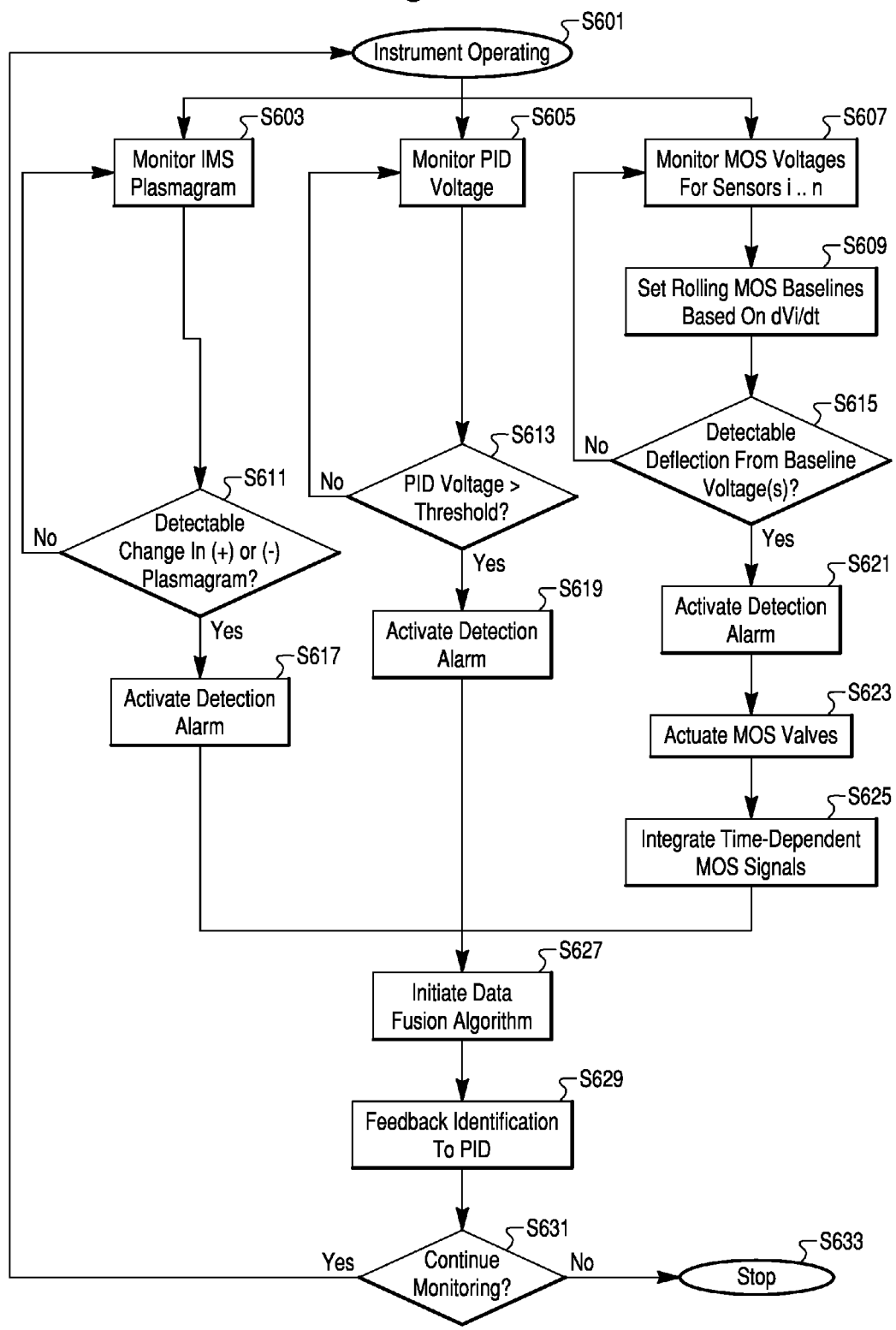
FIG. 6 is a process flow diagram for an exemplary embodiment of a gas identification system using PID, IMS, and MOS array gas analysis units.

An analyte can be identified by analyzing data output from each of the gas analysis technologies. FIG. 6 shows a process flow diagram that can be used by a system to monitor, detect, identify and quantify one or more analytes in a sample. In the embodiment shown in FIG. 6, the gas analysis technologies include a PID, an MOS array, and an IMS. The process flow diagram shows how each of the gas analysis technologies can be controlled independently and how a suite of gas analysis technologies can be used together to detect, identify, and/or quantify an analyte in a sample. For example, in the embodiment shown in FIG. 6, the system is initiated and begins operating (S601), and parameters of the sample are monitored by each of an IMS, PID, and chemical sensor MOS array gas technologies. The IMS monitors an IMS spectrum (S603), the PID monitors voltage (S605), and the MOS array monitors voltages for sensor$_{(i\ldots n)}$ (S607). In conjunction with the monitoring of voltages by the MOS array, rolling MOS baselines based on dVi/dt (change in voltage with time) are set (S609). When the monitored parameter is determined to have reached a threshold amount for any of the gas analysis technologies (S611, S613, S615), a detection alarm may be activated (S617, S619, S621). For example, in the IMS, when a change is detected in a positive or negative phase spectrum an alarm is activated (S617). Similarly, when a PID voltage reaches a specified threshold, an alarm is activated (S619). These alarms can alert the user to a change in the chemical composition of the background atmosphere, and can be a precursor to the subsequent identification step.

The MOS array also monitors for detectable changes in voltage, but can use a rolling baseline (Vo) based on the stability of dVi/dt (S609). A change that results in an alarm (S621) is defined as a detectable deflection from a baseline voltage. This alarm also can alert the user to a change in the chemical composition of the background atmosphere, and is a precursor to the subsequent identification step. The MOS signals can be further processed to convert the time-dependent MOS array signal into a static pattern that can be characteristic of and consistent with a target analyte (S625). Upon activation of the alarm (S621), the valves 32 (See FIGS. 1A and 1B) may be activated to isolate the MOS array (S623), and the time-dependent MOS signals integrated (S625).

If a signal is detected from one or more of the gas analysis technologies (S611, S613, S615) a novel output (or response) data fusion method (S627) can logically sort and filter information from the response data to yield (a) the identity of one or more analytes and the concentration of the analytes, (b) a possible chemical family or list of possible identities for one or more analytes (but no definitive identity) and approximate concentration, and/or (c) an alarm to a detected analyte of unknown identity or class and an approximate concentration. The identification from the data fusion method may be fed back to the PID (S629). In step S631, it is determined whether or not monitoring is to be continued. If not, the monitoring process is stopped (S633). Otherwise monitoring is continued.

Figure 7:
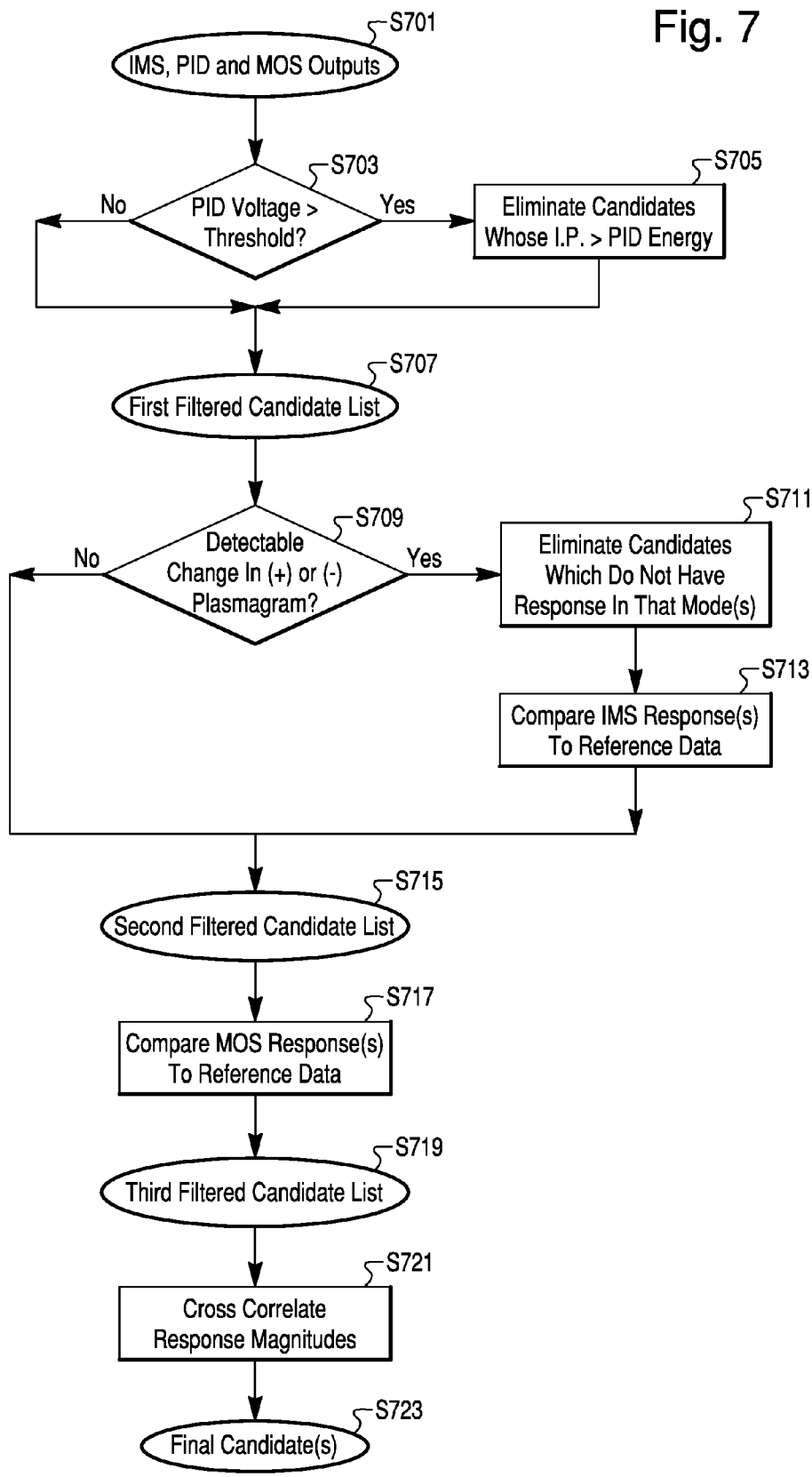
FIG. 7 is a process flow diagram showing detail of a sequential data filtering approach for the "initiate data fusion algorithm" step within the process flow diagram shown in FIG. 6.

FIG. 7 is a process flow diagram that shows an embodiment of a data fusion method (step S627 in FIG. 6). The flow diagram of FIG. 7 shows a "sequential filtering" method of multiplexing the data from more than one gas analysis technology. This method can involve sequential filtering of a target analyte candidate list based on the qualitative aspects, such as, for example, signal shape, peak shape and/or peak position, and the magnitude of output signal (data) from each of the gas analysis technologies. In one embodiment, the qualitative aspects and magnitude of signal output from each of the gas analysis technologies are analyzed and compared with the signal output from the other gas analysis technologies used in a system. The process can involve concatenation of data output from each of the gas analysis technologies that can be followed by analysis of the fused data. The fused data can be analyzed by, for example, principal component analysis (PCA), artificial neural networks (ANN), or any other such pattern recognition and/or hierarchal classification algorithms.

As shown in FIGS. 6 and 7, a system can evaluate each of the gas analysis technology signal outputs independently and in parallel. Analysis of the individual output data can result in a list of "candidate knowns" from each of the gas analysis technologies. Each of the individual candidate lists can be fused to produce the identity or identities of one or more analytes in a target sample. A final identity can be determined based on the comparison of the lists of candidate knowns from each other gas analysis technologies and a statistical analysis of the probabilities that the output signals from the combined gas analysis technologies has the identity of a particular target analyte.

As shown in the exemplary embodiment of FIG. 7, the signal outputs of the gas analysis technologies (IMS, PID and MOS) are provided (S701). In step S703 it is determined whether or not the PID voltage exceeds a threshold amount. Based on this determination, analyte candidates are eliminated (S705), and a first filtered list with the eliminated analyte candidates removed is provided (S707).

In step S709 it is determined whether or not the IMS plasmagram has a detectable change. If so, analyte candidates which do not have such an IMS response are eliminated (S711) from the first filtered list and the IMS response is compared to reference data of the analyte candidates (S713). A second filtered list with the eliminated analyte candidates removed based on the IMS response is provided (S715).

In step 717 the MOS response is compared to reference data of the analyte candidates. Based on this comparison, further analyte candidates may be eliminated from the second filtered list and a third filtered list provided (S719). The response magnitudes from the three gas analysis technologies is then cross-correlated and compared to the reference data from the remaining analyte candidates in the third list (S721) and a final analyte candidate thereby determined (S723).

The process hierarchy can be controlled or facilitated by hardware and software for control of the gas analysis technologies and the detectors and sensors that are comprised in the gas analysis technologies.

Figure 8:
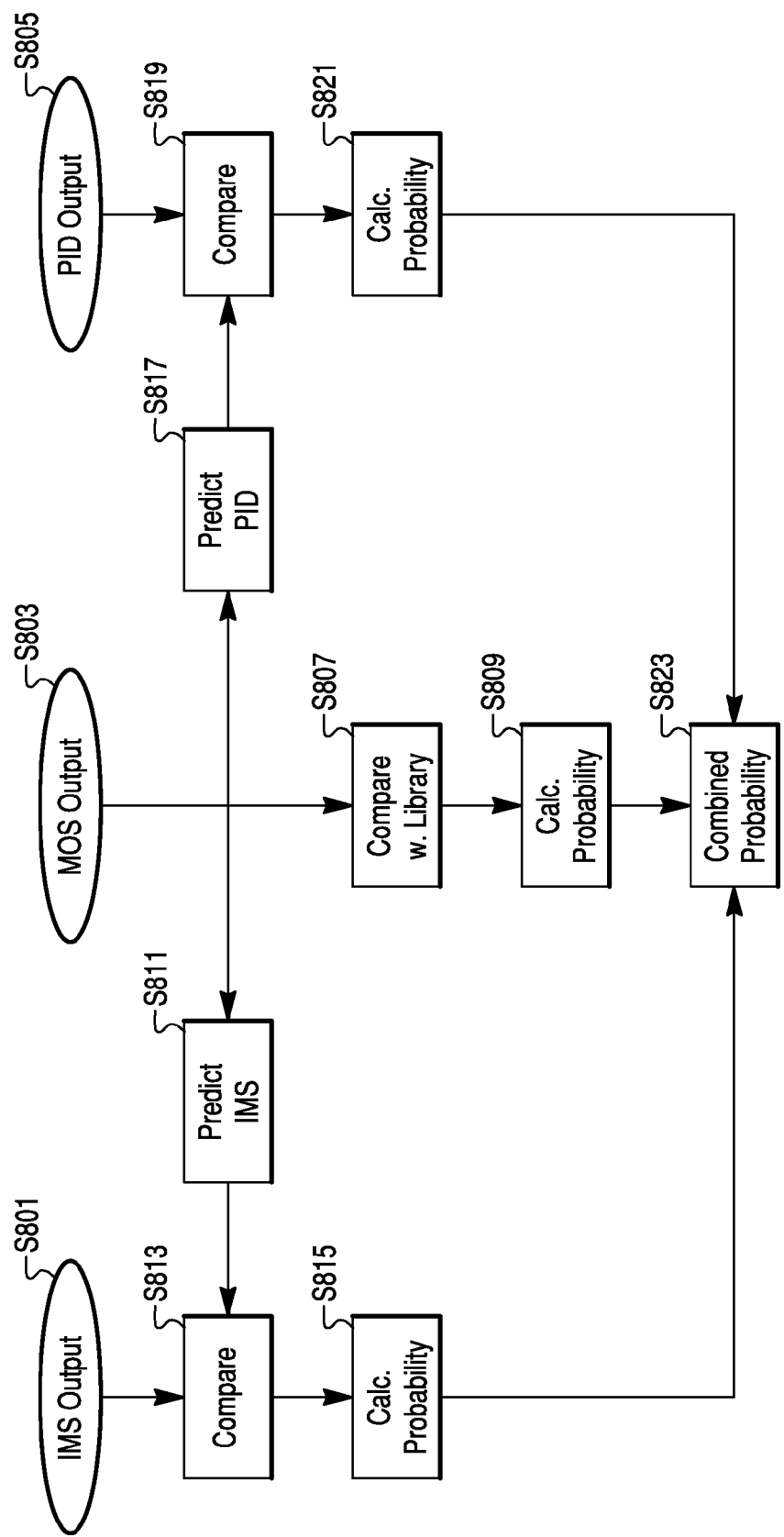
FIG. 8 is a process flow diagram showing detail of a predictive combined probability approach for the "initiate data fusion algorithm" step within the process flow diagram shown in FIG. 6 for another exemplary embodiment.

FIG. 8 illustrates a process flow diagram illustrating another embodiment of a data fusion method as an alternative to the method of FIG. 7. The data fusion method in FIG. 8 is based on probabilities of fit generated from parallel tests. As illustrated in FIG. 8, three different tests are presented but any combination of tests utilizing the data from the three different instruments 20, 30, and 40 (See FIGS. 1A and 1B) might be used. The three tests are based on the responses from the PID, chemical sensor MOS array and IMS, as illustrated by the IMS output step (S801), MOS output step (S803), and PID output step (S805).

The first test presented is a comparison between chemical sensor MOS array response of library entities and the unknown analyte being detected by the chemical sensor MOS array (S807). Based on the closeness of fit, a probability for fit is calculated for each and every entity in the library (S809). The closeness of fit may be determined, for example, using a least squares fit analysis, or some other fit analysis.

The second test uses the chemical sensor MOS array response and quantitatively predicts the PID response at some given time after detection, such as about 10 seconds after detection, for example, for each and every entity in the library (S817). The predicted and a measured PID response are compared (S819). Based on the closeness between predicted and the measured PID response, a probability of fit is calculated for each and every entity in the library (S821). The closeness of fit may be determined, for example, using a least squares fit analysis, or some other fit analysis.

The third presented test uses the chemical sensor MOS array response to predict the IMS response (S811). The predicted and a measured IMS response are compared (S813). Based on closeness of fit, a probability of fit is calculated for each and every entity in the library (S815). The closeness of fit may be determined, for example, using a least squares fit analysis, or some other fit analysis.

The calculated probabilities are combined in some way to produce one combined probability of fit for each and every one of the library entities (S823). The individual probabilities might be combined, for example, using an average, a product, or weighted product, or some other mathematical combination of the probabilities.

Example 1

This example provides details the potential configuration of a gas analysis system. Default settings for all configurable parameters are specified below.

Metal Oxide (MO) Sensors

Six separate TGS style MO sensors are used. The functions performed by the MO sensor array are as follows:

Prior to startup, the output voltage of each sensor (Vi) is checked to determine a "cold" baseline. A change from this baseline upon startup indicates that a sensor is operable. Upon startup, a direct current (DC) heater operating voltage (Vop) is applied to each sensor as specified by VHEATi. (volts, i=1 to 6).

The output of each sensor (Vi) and each time-dependent slope (dVi/dt), as well as temperature and humidity, are continuously monitored at 5 Hz. The sensor path valves are operated to allow exposure of the array to sample by default.

The MO sensors are stable and "ready" when all $dV_i/dt$<DSTABLE for TSTABLE (sec). At this time, each sensor baseline $V_i0$ is remembered as $V_i$. This is used later to determine when sensors are clean. If all sensors remain stable for TSTABLE (and by default have not responded to any sample), the baselines are reset on a rolling basis after each passage of TSTABLE.

The deflection of each sensor output voltage from its baseline ($\Delta V_i = (V_i - V_i0)$, once the initial baseline is established) and the mathematical sum of these deflections ($SUM(\Delta V_i)$) are calculated and continuously monitored at 5 Hz. When the absolute value of $SUM(\Delta V_i)$ DTHRESH1, the sensor path valves are actuated to isolate the sensors for time TVALVE1 (seconds).

After TVALVE1 elapses the sensor path valves are actuated to allow the array to clear out for TVALVE2 (sec). If after this time $[\Delta\{SUM(\Delta V_i)\}]>0$ indicating that additional sample is reaching the sensor array, the valves are actuated to isolate the array again. This process is repeated until $[\Delta\{SUM(\Delta V_i)\}]<0$, indicating that clean air is passing through the system and the sensor path can remain exposed to recover.

At time TIME1 after DTHRESH1 is met, the $V_i$'s are read and the logarithmic transform of the ratio ($V_i0/V_i$) is computed. The MO sensor pattern is a 6-channel array of the logarithmic transform. Data from this array is processed, for example, by the data fusion algorithm illustrated in FIG. 7 or 8.

After the sensor isolation valves have been opened and the sensors have recovered to baseline, they area "ready" again when all $dV_i/dt$<DSTABLE for TSTABLE and each $V_i$ is within +/−VBASE volts of its original $V_i0$. The PID and IMS operate in a "continuous monitor" mode during this time.

Based on the MO response, the user will see one of the following:

"Ready" indication based on $dV_i/dt$ meeting the DSTABLE condition (and $V_i$ meeting VBASE condition after sample cleardown).

"Detect" indication based on $SUM(\Delta V_i)$ meeting the DTHRESH1 condition.

"Identity" based on array processing and subsequent multiplexing with other detector outputs.

Default parameter values for the system are:
DSTABLE=0.011
TIME1=10.0 sec
TSTABLE=30.0 sec
VHEATi=5.0 V (for all 6 sensors)
DTHRESH1=1.0
TVALVE1=10.0 sec
TVALVE2=1.0 sec
VBASE=0.3 volts Photoionization Detector (PID)

One 10.6 eV PID sensor is used. The functions performed by the PID are as follows:

The PID is "ready" immediately upon startup. An electronic check is used to ensure the PID is operable. The raw Vout (volts) is continuously monitored at 1 Hz (or optimum rate based on A/D delay times).

The PID A/D has a settable gain PIDGAIN, with available values of 1, 4, 8, 16, 32, or 64.

The baseline voltage PID0 (volts) is set upon user calibration or autonomously by the system, and the calibration factor PIDCAL (volts/ppm) is supplied by the manufacturer but is user-updatable upon calibration.

The system continuously computes sample concentration as $[((Vout-PID0)/PIDCAL)*CF]$. Note that the default CF=1.0 for isobutylene (calibrant gas), and the readout is denoted as "Isobutylene Units" until the sample is identified.

A PID response detected above (PID0+PIDTHRESH) is used to set a binary metric ("Detect"=1 or "No Detect"=0) for filtering the chemical identity hit lists when the output is multiplexed with the MOS and IMS outputs.

Based on the PID response, the user will see:
"Ready" indication based on successful power up
"Detect" indication based on rise in signal that is PIDTHRESH above the baseline PID0
"PPM Isobutylene" prior to sample identification
"PPM [sample]" after the sample is identified and its CF is recalled from the system computer
Default parameter values for the PID are:
PIDGAIN=1
PIDCAL=volts/ppm, set for each unit
CF=1.0 (Isobutylene)
PIDTHRESH=0.002 volts Ion Mobility Spectrometer (IMS)

The system can include one IMS detector (Smiths Detection), which operates as configured by its manufacturer.

The IMS generates a table of $k_0$ versus intensity (counts) for each of the positive and negative mode IMS spectra (collected at 0.2 Hz). This table is compared against predefined compound "windows" to determine whether the signal is consistent with a known compound, and this information is multiplexed with the MOS and PID to arrive at a final sample identity (FIG. 7 or 8).

Based on the IMS response, the user will see:
"Ready" indication based on successful power up (status reported by the IMS)
"Detect" indication based on presence of a peak or peaks in either the positive and/or negative modes
"Identity" based on processing the $k_0$ table against the sample windows and multiplexing this information with the MOS and PID outputs.

Example 2

To validate the multi-detector gas identification system, experiments are conducted with several toxic industrial chemical (TIC) gases and vapors. A hardware prototype of the system as described herein is constructed with all components connected on a common sample flow path. The IMS is controlled using custom software (Smiths Detection). The PID and MOS are controlled using a custom interface written in LabVIEW™ (National Instruments, Austin, Tex.). The raw MOS time-dependent data is converted to array patterns using Origin™ (OriginLab, Northampton, Mass.) and Fortran (Open Watcom). The data fusion algorithm is coded and executed using Fortran.

This example characterizes twenty one TICs using the multi-detector gas analysis system. Each compound is studied over a range of gas phase concentrations (in parts-per-million, ppm) above and below its Immediately Dangerous to Life and Health (IDLH) value under flowing conditions. For gases, certified mixtures in a nitrogen balance (Scott Specialty Gas, South Plainfield, N.J.) are combined with pure zero air (Scott) using digital mass flow controllers (Sierra Instruments, Monterey, Calif.) to attain the desired dilutions. For vapors, pure liquids (Sigma-Aldrich, St. Louis, Mo.) are delivered with a syringe driver (Cole-Parmer, Vernon Hills, Ill.) into a balance of zero air. Humidification is achieved by flowing zero air through a gas washing bottle (Fisher Scientific, Hampton, N.H.) and combining the flow with the sample stream. Humidities range from 0-50% R.H. and all measurements are conducted at room temperature. A sample delivery system is configured to maintain a consistent humidity and flow rate (typically 2-10 standard liters per minute, slpm) for the background and sample air streams. Both streams are kept flowing at all times and are switched between instrument and exhaust via a four-way valve.

To measure a sample, the instrument is first turned on and allowed to stabilize in the presence of the background air stream of the desired humidity. During this time, the sample stream of the desired TIC concentration is established and directed to exhaust. Introduction of the sample is achieved by turning the four-way valve toward the instrument for a preset time (typically 10 seconds). Replicate measurements are collected to evaluate reproducibility.

Result: Acetone

In this example, an "unknown" sample of acetone vapor is measured at 50 ppm (1/50 IDLH) and 50% R.H. at ambient temperature. Upon exposing the instrument to the vapor, only the PID and MOS detectors respond. Based on these detection events, the data fusion algorithm of FIG. 7 is initiated. Since the PID responds, twelve of the twenty one candidate TICs are eliminated in the first filter step, because their ionization potentials (I.P.) are greater than the 10.6 eV PID bulb energy. Therefore, nine TICs remain in the first filtered candidate list. Of these compounds, none are eliminated in the second filter, because the IMS produced no response and an IMS-active TIC could be present below its detectable concentration. This leaves nine TICs in the second filtered candidate list.

The MOS array patterns for these candidates are then compared to the sample pattern in the third filter step, leaving three compounds in the third candidate filter list: acetone, ethanol and hydrogen sulfide. To discriminate among these three possibilities, the magnitudes of the various detector responses are then cross-correlated on a case-by-case basis.

According to the PID response, the unknown sample concentration corresponds to 38 ppm isobutylene (the calibrant gas). In general, the PID concentrations obtained in these measurements are always less than the equilibrium reference measurements, since the PID readings are taken shortly after each detection event before the sample stabilizes within in the flow path (see FIG. 4). The data fusion algorithm incorporates an empirical adjustment factor to account for this discrepancy. However, the PID concentrations reported to the user during continuous operation are real-time, unadjusted values. This translates into 42 ppm acetone, 380 ppm ethanol, or 125 ppm hydrogen sulfide based on the respective PID correction factors for these candidates. The magnitude of the MOS pattern, determined as the sum of the individual channel signals, is 14 V. This translates into 50 ppm acetone, 40 ppm ethanol, or 100 ppm hydrogen sulfide. Clearly, the magnitudes of the PID and MOS are only consistent with acetone or hydrogen sulfide, so ethanol is eliminated as a plausible candidate.

The lack of response at the IMS detector is then considered for further discrimination. If acetone were present at 50 ppm (based on the MOS array) it would not produce a spectrum, because its IMS detection limit is 100 ppm. However, 125 ppm of hydrogen sulfide would produce a distinct negative mode response as its detection limit is <1 ppm. This inconsistency eliminates hydrogen sulfide as a plausible candidate, so acetone is reported as the identity of the sample. The results of this analysis are summarized in TABLE 1.

TABLE 1

Analysis of 50 ppm acetone with multi-detector system prototype and data fusion algorithm based on sequential filtering. The calculated concentrations for candidates from the third filtered list are derived from the individual detector measurements and used for the magnitude cross-correlation step.

| Initiate algorithm Full Candidate List | PID = YES 38 ppm isobutylene* First Filtered List | IMS (+) = NO IMS (−) = NO Second Filtered List | MOS = YES Σ = 14 V Third Filtered List | Cross Correlate Magnitudes Final Candidate(s) |
|---|---|---|---|---|
| acetone | acetone (42 ppm) | acetone (<100 ppm) | acetone (50 ppm) | acetone |
| acrolein | acrolein | acrolein | ethanol (40 ppm) | |
| acrylonitrile | ammonia | ammonia | hydrogen sulfide (100 ppm) | |
| ammonia | benzene | benzene | | |
| benzene | carbon disulfide | carbon disulfide | | |
| carbon disulfide | ethanol (380 ppm) | ethanol (<500 ppm) | | |
| chlorine | ethylene oxide | ethylene oxide | | |
| diborane | hydrogen sulfide (125 ppm) | hydrogen sulfide (<1 ppm) | | |
| ethanol | phosphorous trichloride | phosphorous trichloride | | |
| ethylene oxide | | | | |
| fluorine | | | | |
| formaldehyde | | | | |
| hydrogen chloride | | | | |
| hydrogen cyanide | | | | |
| hydrogen fluoride | | | | |
| hydrogen sulfide | | | | |
| nitric acid | | | | |
| phosgene | | | | |
| phosphorous trichloride | | | | |
| propane | | | | |
| sulfur dioxide | | | | |

*Modified by empirical adjustment factor described in text

Result: Acrylonitrile

An "unknown" sample of acrylonitrile vapor also is measured at 8 ppm (1/10 IDLH) and 50% R.H. This time, only the MOS detector responds. Following the data fusion algorithm based on sequential filtering, no candidates are eliminated in the first filter, because a lack of PID response could have meant that a PID-active compound (with I.P.<10.6 eV) is present below the detection limit. The same is true for the IMS filter, so all candidates are retained in the second filtered list. The sample MOS pattern is therefore compared against all of the reference patterns, and four candidates remain: acrylonitrile, diborane, ethanol and hydrogen sulfide. To discriminate among these four possibilities, the magnitudes of the various detector responses are then cross-correlated on a case-by-case basis.

For this sample, the MOS sum is 3.8 V. For the candidates in the third filtered list, this corresponds to 9 ppm acrylonitrile, 1 ppm diborane, 10 ppm ethanol or 1 ppm hydrogen sulfide. Because acrylonitrile is not PID- or IMS-active, it would not produce a response at either detector as observed in this measurement, so it remains a candidate. Diborane is not PID-active either, but its IMS detection limit is 0.5 ppm, so it would produce a negative mode response. Conversely, ethanol is not IMS-active but does have a PID response, and it would have produced a PID signal at 10 ppm. As such, these two compounds are eliminated as plausible candidates. Finally, hydrogen sulfide has both a PID and an IMS response, but at the 1 ppm concentration level suggested by the MOS detector, it would be expected to produce signals at all devices. Therefore, hydrogen sulfide is eliminated from consideration and acrylonitrile is reported as the only TIC likely to produce the observed signals. The results of this analysis are reported in TABLE 2.

This example represents a large set of experimental measurements that have been conducted to validate the multi-detector hardware platform and data fusion algorithm for gas and vapor identification. These results demonstrate the importance of combining orthogonal detection techniques and the power of evaluating quantitative information to corroborate qualitative responses of the associated devices for sample identification.

What is claimed is:

1. A method for determining the presence of one or more specific chemicals in a sample of gas, the method comprising:
   receiving a first response signal characteristic of the presence or absence of at least one first chemical or group of chemicals in a sample of gas, the first response signal generated by a photoionization detector;
   receiving a second response signal characteristic of the presence or absence of at least one second chemical or group of chemicals in the sample of gas, the second response signal generated by an ion mobility spectrometer;
   receiving a third response signal characteristic of the present or absence of at least one third chemical or group of chemicals in a sample of gas, the third response signal generated by a chemical sensor array;
   analyzing the first response signal to generate a first list of candidate chemicals for the sample of gas;
   analyzing the second response signal to generate a second list of candidate chemicals for the sample of gas;

TABLE 2

Analysis of 8 ppm acrylonitrile with multi-detector system prototype and data fusion algorithm based on sequential filtering. The calculated concentrations for candidates from the third filtered list are derived from the individual detector measurements and used for the magnitude cross-correlation step.

| Initiate algorithm Full Candidate List | PID = NO First Filtered List | IMS (+) = NO IMS (−) = NO Second Filtered List | MOS = YES Σ = 3.8 V Third Filtered List | Cross-Correlate Magnitudes Final Candidate(s) |
|---|---|---|---|---|
| acetone | acetone | acetone | acrylonitrile (9 ppm) | acrylonitrile |
| acrolein | acrolein | acrolein | diborane (1 ppm) | |
| acrylonitrile | acrylonitrile | acrylonitrile | ethanol (10 ppm) | |
| ammonia | ammonia | ammonia | hydrogen sulfide (1 ppm) | |
| benzene | benzene | benzene | | |
| carbon disulfide | carbon disulfide | carbon disulfide | | |
| chlorine | chlorine | chlorine | | |
| diborane | diborane | diborane (<0.5 ppm) | | |
| ethanol | ethanol (<10 ppm) | ethanol (<500 ppm) | | |
| ethylene oxide | ethylene oxide | ethylene oxide | | |
| fluorine | fluorine | fluorine | | |
| formaldehyde | formaldehyde | formaldehyde | | |
| hydrogen chloride | hydrogen chloride | hydrogen chloride | | |
| hydrogen cyanide | hydrogen cyanide | hydrogen cyanide | | |
| hydrogen fluoride | hydrogen fluoride | hydrogen fluoride | | |
| hydrogen sulfide | hydrogen sulfide (<0.3 ppm) | hydrogen sulfide (<1 ppm) | | |
| nitric acid | nitric acid | nitric acid | | |
| phosgene | phosgene | phosgene | | |
| phosphorous trichloride | phosphorous trichloride | phosphorous trichloride | | |
| propane | propane | propane | | |
| sulfur dioxide | sulfur dioxide | sulfur dioxide | | | analyzing the third response signal to generate a third list of candidate chemicals for the sample of gas; and causing a processor to fuse the first, second, and third lists of candidate chemicals to generate information indicative of the presence of one or more specific chemicals in the sample of gas.

2. The method as recited in claim 1, further comprising individually controlling operation of the photoionization detector, the ion mobility spectrometer, and the chemical sensor array to cause the photoionization detector to autonomously monitor the sample of gas to generate the first response signal, to cause the ion mobility spectrometer to autonomously monitor the sample of gas to generate the second response signal, and the cause the chemical sensor array to autonomously monitor the sample of gas to general the third response signal.

3. The method as recited in claim 1, further comprising using the generated information indicative of the presence of the one or more chemicals or groups of chemicals in the sample of gas to furnish a correction to at least one of the photoionization detector, the ion mobility spectrometer, and the chemical sensor array.

4. The method as recited in claim 1, wherein at least one of analyzing the first response signal, analyzing the second response signal, and analyzing the third response signal comprises comparing a response furnished by the first response signal, the second response signal, or the third response signal with a library of known responses to identify candidate chemicals.

5. The method as recited in claim 4, further comprising determining a closeness of fit of the response to at least one known response of the library of known responses to determine a probability that a candidate chemical having the known response is present in the sample of gas.

6. The method as recited in claim 1, wherein analyzing the second response signal generated by the ion mobility spectrometer comprises using a response furnished by the second response signal to generate an ion spectrum having peak intensities and comparing the peak intensities against known peak windows of candidate chemicals to identify a candidate chemical.

7. The method as recited in claim 1, wherein the third response signal generated by the chemical sensor array comprises a time-dependent voltage, and wherein analyzing the third response signal comprises using pattern recognition to detect a pattern in the time-dependent voltage that is characteristic of a candidate chemical.

8. The method as recited in claim 1, wherein the first response signal generated by the photoionization detector comprises a voltage output, and wherein analyzing the first response signal comprises generating a binary metric indicating whether a candidate chemical is present according to a known ionization potential of the candidate chemical.

9. The method as recited in claim 1, wherein the chemical sensor array is a metal oxide chemical sensor array.

10. A non-transient computer-readable storage medium having computer executable instructions for determining the presence of one or more specific chemicals in a sample of gas, the computer executable instructions comprising:

individually controlling operation of a photoionization detector, a ion mobility spectrometer, and a chemical sensor array to cause the photoionization detector to monitor a sample of gas to generate a first response signal characteristic of the presence or absence of at least one first chemical or group of chemicals in the sample of gas, to cause the ion mobility spectrometer to monitor the sample of gas to generate a second response signal characteristic of the presence or absence of at least one second chemical or group of chemicals in the sample of gas, and to cause the chemical sensor array to monitor the sample of gas to generate a third response signal characteristic of the presence or absence of at least one third chemical or group of chemicals in the sample of gas;

analyzing the first response signal to generate a first list of candidate chemicals for the sample of gas;

analyzing the second response signal to generate a second list of candidate chemicals for the sample of gas;

analyzing the third response signal to generate a third list of candidate chemicals for the sample of gas; and fusing the first, second, and third lists of candidate chemicals, to generate information indicative of the presence of one or more specific chemicals in the sample of gas.

11. The computer-readable storage medium as recited in claim 10, wherein individually controlling operation of the photoionization detector, the ion mobility spectrometer, and the chemical sensor array comprises causing the photoionization detector to be operated using a first set of operation parameters, causing the ion mobility spectrometer to be operated using a second set of operation parameters, and causing the chemical sensor array to be operated using a third set of operation parameters, to monitor the sample of gas.

12. The computer-readable storage medium as recited in claim 10, wherein the computer executable instructions further comprise using the generated information indicative of the presence of the one or more chemicals in the sample of gas to furnish a correction to at least one of the photoionization detector, the ion mobility spectrometer, and the chemical sensor array.

13. The computer-readable storage medium as recited in claim 10, wherein at least one of analyzing the first response signal, analyzing the second response signal, and analyzing the third response signal comprises comparing a response furnished by the first response signal, the second response signal, or the third response signal with a library of known responses to identify candidate chemicals.

14. The computer-readable storage medium as recited in claim 13, wherein the computer executable instructions further comprise determining a closeness of fit of the response to at least one known response of the library of known responses to determine a probability that a candidate chemical having the known response is present in the sample of gas.

15. The computer-readable storage medium as recited in claim 10, wherein analyzing the second response signal generated by the ion mobility spectrometer comprises using a response furnished by the second response signal to generate an ion spectrum having peak intensities and comparing the peak intensities against known peak windows of candidate chemicals to identify a candidate chemical.

16. The computer-readable storage medium as recited in claim 10, wherein the third response signal generated by the chemical sensor array comprises a time-dependent voltage, and wherein analyzing the third response signal comprises using pattern recognition to detect a pattern in the time-dependent voltage that is characteristic of a candidate chemical.

17. The computer-readable storage medium as recited in claim 10, wherein the first response signal generated by the photoionization detector comprises a voltage output, and wherein analyzing the first response signal comprises generating a binary metric indicating whether a candidate chemical is present according to a known ionization potential of the candidate chemical.

18. The computer-readable storage medium as recited in claim 10, wherein the chemical sensor array is a metal oxide chemical sensor array.

19. A system comprising:
- a plurality of gas analysis units configured to be in fluid communication with a common sample of gas, the plurality of gas analysis units comprising a photoionization detector configured to generate a first response signal characteristic of the presence or absence of one or more chemicals in the gas sample, an ion mobility spectrometer configured to generate a second response signal characteristic of the presence or absence of one or more chemicals in the gas sample, and a chemical sensor array configured to generate a third response signal characteristic of the presence or absence of one or more chemicals in the gas sample; and
- a processor configured to:
  - analyze the first response signal to generate a first list of candidate chemicals for the sample of gas;
  - analyze the second response signal to generate a second list of candidate chemicals for the sample of gas;
  - analyze the third response signal to generate a third list of candidate chemicals for the sample of gas; and
  - fuse the first, second, and third lists of candidate chemicals to generate information indicative of the presence of one or more specific chemicals in the sample of gas.

20. The system as recited in claim 19, wherein the processor is configured to independently control operation of respective ones of the photoionization detector, the ion mobility spectrometer, and the chemical sensor array using operational parameters appropriate for causing operation of the photoionization detector, the ion mobility spectrometer, and the chemical sensor array to monitor the sample of gas.

21. The system as recited in claim 20, wherein the processor is configured to cause respective ones of the photoionization detector, the ion mobility spectrometer, and the chemical sensor array to discontinue monitoring of the sample of gas when a determination is made that the photoionization detector, the ion mobility spectrometer, and the chemical sensor array have produced a response signal that is sufficient for analysis to identify a list of candidate chemicals for the sample of gas.

22. The system as recited in claim 21, wherein the processor is configured to cause a valve to operate to isolate at least one of the photoionization detector, the ion mobility spectrometer, and the chemical sensor array from becoming saturated by at least a portion of the sample gas.

23. The system as recited in claim 19, wherein the processor is configured to furnish a correction to at least one of the photoionization detector, the ion mobility spectrometer, and the chemical sensor array, the correction derived from the generated information indicative of the presence of the one or more specific chemicals in the sample of gas.

24. The system as recited in claim 19, further comprising a sensor configured to monitor a physical condition of the sample of gas.

25. The system as recited in claim 24, wherein the sensor comprises a relative humidity sensor.

26. The system as recited in claim 19, wherein analyzing the second response signal generated by the ion mobility spectrometer comprises using a response furnished by the second response signal to generate an ion spectrum having peak intensities and comparing the peak intensities against known peak windows of candidate chemicals to identify a candidate chemical.

27. The system as recited in claim 19, wherein the third response signal generated by the chemical sensor array comprises a time-dependent voltage, and wherein analyzing the third response signal comprises using pattern recognition to detect a pattern in the time-dependent voltage that is characteristic of a candidate chemical.

28. The system as recited in claim 19, wherein the first response signal generated by the photoionization detector comprises a voltage output, and wherein analyzing the first response signal comprises generating a binary metric indicating whether a candidate chemical is present according to a known ionization potential of the candidate chemical.

29. The system as recited in claim 19, wherein the chemical sensor array is a metal oxide chemical sensor array.

* * * * *